United States Patent
Calik et al.

(10) Patent No.: US 12,344,848 B2
(45) Date of Patent: Jul. 1, 2025

(54) MODIFIED AOX1 PROMOTER VARIANTS

(71) Applicant: ORTA DOGU TEKNIK UNIVERSITESI, Ankara (TR)

(72) Inventors: Pinar Calik, Ankara (TR); Burcu Gunduz Ergun, Ankara (TR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 957 days.

(21) Appl. No.: 17/276,168

(22) PCT Filed: Sep. 23, 2019

(86) PCT No.: PCT/TR2019/050783
§ 371 (c)(1),
(2) Date: Mar. 15, 2021

(87) PCT Pub. No.: WO2020/068018
PCT Pub. Date: Apr. 2, 2020

(65) Prior Publication Data
US 2022/0033832 A1 Feb. 3, 2022

(30) Foreign Application Priority Data
Sep. 24, 2018 (TR) .................. 2018/13790

(51) Int. Cl.
*C12N 15/81* (2006.01)
(52) U.S. Cl.
CPC .................. *C12N 15/815* (2013.01)
(58) Field of Classification Search
CPC .................................................. C12N 15/815
See application file for complete search history.

(56) References Cited

U.S. PATENT DOCUMENTS

| | | | |
|---|---|---|---|
| 6,730,499 B1 | 5/2004 | Cregg | |
| 7,816,509 B2 | 10/2010 | Lee et al. | |
| 8,222,386 B2 | 7/2012 | Cregg et al. | |
| 8,785,613 B2 | 7/2014 | Cregg et al. | |
| 9,279,129 B2 | 3/2016 | Hartner et al. | |
| 2011/0012987 A1 | 1/2011 | Yoon | |
| 2012/0164205 A1* | 6/2012 | Baum | C12N 15/8286 435/254.11 |

FOREIGN PATENT DOCUMENTS

| | | | |
|---|---|---|---|
| WO | WO-2006089329 A2 * | 8/2006 | .......... C12N 15/815 |
| WO | 2017021541 A1 | 2/2017 | |

OTHER PUBLICATIONS

Franz S. Hartner, et al., Promoter library designed for fine-tuned gene expression in Pichia pastoris. Nucleic Acids Research, 2008, pp. e76-e76, vol. 36 No. 12.
Joseph Sambrook, et al., Molecular cloning: a library manual, 2001, pp. 1.116-1.118, 3rd ed., vol. 1, Cold Spring Harbor Library Press, New York.
Mudassar Ahmad, et al., Protein expression in Pichia pastoris: recent achievements and perspectives for heterologous protein production, Applied Microbiology and Biotechnology, 2014, pp. 5301-5317, vol. 98 No. 12.
Cheng Cheng, et al., Identification of Potential Target Genes for Adr1p through Characterization of Essential Nucleotides in UAS1, Mol. Cell. Biol., 1994, pp. 3842-3852., vol. 14.
Stephanie Roth, et al., Transcriptional activators Cat8 and Sip4 discriminate between sequence variants of the carbon source-responsive promoter element in the yeast *Saccharomyces cerevisiae*, Current Genetics, 2004, pp. 121-128, vol. 45 No. 3.
Invitrogen, EasySelect™ Pichia Expression Kit For Expression of Recombinant Proteins Using pPICZ and PPICZα in Pichiapastoris, User Manual, 2010, pp. 1-86, Cat. No. K1740-01.

\* cited by examiner

*Primary Examiner* — Kevin K Hill
*Assistant Examiner* — Allison Marie Johnson
(74) *Attorney, Agent, or Firm* — Bayramoglu Law Offices LLC

(57) ABSTRACT

*Pichia pastoris* alcohol oxidase 1 (AOX1) promoter variants include at least one of the specified modifications on wild-type *Pichia pastoris* AOX1 promoter (SEQ ID NO: 1). The modifications include the following: a) integration of a Cat8 transcription factor binding site (TFBS), particularly integration of SEQ ID NO: 6 or SEQ ID NO: 7 or other gene sequences that show at least 80% similarity with these sequences, at any position within nucleotides 94 to 110, 141 to 160, 312 to 330, 355 to 380, 501 to 521; 640 to 658, 674 to 693, and 1 to 840; b) integration of Aca1 or Aca2 TFBS particularly integration of SEQ ID NO: 8 or other gene sequences showing at least 80% similarity with this sequence at any position between the nucleotides 1 to 840; c) mutations specified with SEQ ID NO: 2 within nucleotides 94 to 693 and combinations thereof.

18 Claims, 6 Drawing Sheets
Specification includes a Sequence Listing.

SEQUENCE NO 1

> P_{AOX1-wt}

AGATCTAACATCCAAAGACGAAAGGTTGAATGAAACCTTTTGCCATCCGACATCCACAGGTCCATTCTC
ACACATAAGTGCCAAACGCAACAGGAGGGATACACTAGCAGACGTTGCAAACGCAGGACCTCC
ACTCCTCTCTCCTCAACACCCACTTTTGCCATCGAAAACCAGCCCAGTTATTGGGCTTGATTGGAGCT
CGCTCATTCCAATTCCTTCTATTAGCTACTAACACCATGACTTTATTAGCTGTCTATCCTGGCCCCCTG
GCGAGGTTCATGTTTATTTCCGAATGCAACAAGTCCGCATTACACCGAACATCACTCAGATGA
GGGCTTTCTGAGTGTGGGGTCAAATAGTTTCATGTTCCCCAAATGCCCAAAACTGACAGTTAAACGC
TGTCTTGGAACCTAATATGACAAAAGCGTGATCTCATCCAAGATGAACTAAGTTTGGTTCGTTGAAATGCT
AACGGCCAGTTGGTCAAAAGAAACTTCCAAAAGTCGGCATACCGTTTGTCTGTTGGTATTGATTGAC
GAATGCTCAAAATCTCATTAATGCTCAGTCTCTATCGTTCTGAACCCCGGTGCACCTGT
GCCGAAACGCAAATGGGGAAACACCCGCTTTTGGATGATTATGCATTGTCTCCACATGTATGCTTCCA
AGATTCTGGTGGGAATACTGCTGATAGCCTAAACGTTCATGATCAAAATTAACTGTTCTAACCCTACTTG
ACAGCAATATAAACAGAAGGAAGCTGCCCTGTCTTAAACCTTTTTTTATCATCATTATTAGCTTACTT
TCATAATTGGCGACTGGTTCCAATTGACAAGCTTTTGATTTTAACGACTTTTAACGACAACTTGAGAAGATC
AAAAAACAACTAATTATTCGAAACG

FIG. 2

SEQUENCE NO 2
> P<sub>AOX1-mod</sub> (P<sub>mAOX1</sub>)
AGATCTAACATCCAAAGACGAAAGGTTGAATGAAACCTTTTGCCATCCGACATCCACAGGTCCATTCTCACAC
ATAAGTGCCAAACGCAACAAATTCCGTTCGTCCGATTAGCAGACCTTGCAAACGACCTCCACACCCCAA
TATTATTTGGGGTACTTTTGCCATCGAAAAACCAGCCCAGTTATTGGGTTGATTGGAGCTGCTCATTCCAATT
CCTTCTATTAGGCTACTAACCATGACTTATTAGCCTGTCTATCCTGGCCCCCTGGCGAGTTCATGTTTGTT
TATTCCGAATGCCCTCTCGTCCGGGCTTTTTCCGAACATCACTCCAGATGAGGGGGACCCCACATTTTTTT
GACCCCACATGTTCCCAAATGGCCCAAACTAAGTTAAACGTCGTCTTGGAACTAATATGACAAAAGCG
TGATCTCATCCAAGATGAACTAAGTTGGTTCGTTGAAATGCTAACGGCCAGTGCCTATTGTAGACGTCAACCC
AAGTCGGCATACCGTTTGTCTTGTTTGGTATTGATTGACGAAGTGCTCAAAATAATCTCATTAATGCTTAGGCA
GTCTCTCTATCGCTTCTGAACCCTGTGCCGAAACATATATTCCGTTCGTCCGAATCTTTTTGGATGAT
TAACCCCAATACATTTTGGGGTTGCTCCAAGATTCGGTGGGAATACTGCTGATAGCCTAACGTTCATGATCAA
AATTTAACTGTTCTAACCCTACTTGACAGCAATATATAAACAGAAGGAAGCTGCCCTGTCTTAAACCTTTTTTT
TATCATCATTATTAGCTTACTTTCATAATTGCGACTGGTTCCAATTGACAAGCTTTTGATTTAACGACTTTAAGG
ACAACTTGAGAAGATCAAAAACAACTAATTATTCGAAACG

* Modified positions in the design of AOX1 promoter variants are represented with bold and underlined characters.

FIG. 3

SEQUENCE NO 3

> P$_{AOX1-Cat2}$ (P$_{AOX1/Cat8-L2}$)
AGATCTAACATCCAAAGACGAAAGGTTGAATGAAACCTTTTGCCATCCGACATCCACAGGTCCATTCTCACACA
TAAGTGCCAAACGCAACAGGAGGGGATACACTAGCAGCAGGACCGTTGCAAACGCAGGACCTCCACTCCTCTTC
TCCTCAACACCACTTTTGCCATCGAAAAACCAGCCCAGTATTGGGCTTGATTGGAGCTCGCTCATTCCAATTC
CTTCTATTAGGCTACTAACACCATGACTTTATTAGCCTGTCTATCCTGGCCCCCCCTGGCGAGGTTCATGTTGTTTA
TTTCCGAATGCCCTCTCGTCCGGGCTTTTCCGAACATCACTCCAGATGAGGGCTTTCTGAGTGTGGGGTCAAA
TAGTTTCATGTTCCCCAAATGGCCCAAAACTGACAGTTTAAACGCGTGTCTTGGAACTAATATGACAAAGCGTG
ATCTCATCCAAGATGAACTAAGTTTGGTTCGTTGAAATGCTAACGGCCAGTTGGTCAAAAAGAAACTTCCAAAA
GTGGGCATACCGTTTGTCTTGTTTGGTATTGATTGACGAACATGCTCAAAATAATCTCATTAATGCTTAGGCAGTC
TCTCTATCGCTTCTGAACCCGGTGTCCGAAACTGTGCCGAAACGCAACACCCGCTTTTGGATGATTAT
GCATTGTCTCCACATGTATGCTTCCAAGATTCGATAGCCTAAGTTCATGATCAAAATT
TAACTGTTCTAACCCCTACTTGACAGCAATATAAACAGAAGAAGCTGCCCGTGTCTTAAACCTTTTTTTATCA
TCATTATTAGCTTACTTCATAATTGCGACTGGTTCCAATTGACAAGCTTTGATTTAACGACTTTTAACGACAAC
TTGAGAAGATCAAAAACAACTAATTATTCGAAACG

* Modified positions in the design of AOX1 promoter variants are represented with bold and underlined characters.

FIG. 4

SEQUENCE NO 4
> P_AOX1-Cat3 (P_AOX1/Cat8-L3)
AGATCTAACATCCAAAGACGAAGGTTGAATGAAACCTTTTGCCATCCGACATCCACAGGTCCATTCTCACACATAAG
TGCCAAACGCAACAGGAGGGGATACACTAGCAGCAGACGTTGCAAAGCAGGACCTCCACTCCTCTCCTCAACA
CCCACTTTTGCCATCGAAAAACCAGCCAGTTATTGGGCTTGATTGGAGCTCGCTCATTCCAATTCCTTCTATTAGGCTA
CTAACACCATGACTTTATTAGCCTGCTGTCTATCCTGGCCCCCCGGCGAGGTTCATGTTGTTTATTTCCGAATGCAACAAG
CTCCGGCATTACACCCGAACATCACTCCAGATGAGGGCTTTCTGAGTGTGGGGTCAAATAGTTTCATGTTCCCAAATGG
CCCAAAACTGACAGTTTAAACGCTGTCTTGGAACCTAATATGACAAAGCGTGATCTCATCCAAGATGAACTAAGTTTG
GTTCGTTGAAATGCTAACGGCCAGTTGGTCAAAAAGAAACTTCCAAAAGTCGGCATACCGTTTGTCTTGTTTGGTATTG
ATTGACGAATGCTCAAAAATCTAGGCGACAGTCTCTATCGCTTCTGAACCCGGTGCACCTGTGCC
GAAACATATTCCGTTCGTCGAATCTTTTTGGATGATTATGCATTGTCTCCACATTGTTCTCCAAGATTGTCGGTGGGA
ATACTGCTGATAGCCTAACGTTCATGATCAAAATTTAACTGTTCTAACCCTACTTGACAGCAATATAAACAGAAGGAA
GCTGCCCTGTCTAAACCTTTTTTTTATCATCATTAGCTACTTCATAATTGCGACTGGTTCCAATTGACAAGCTTT
TGATTTAAGCACTTTTAACGACATTGAGAAGATCAAAAAAACAACTAATTATTCGAAACG

* Modified positions in the design of AOX1 promoter variants are represented with bold and underlined characters.

FIG. 5

SEQUENCE NO 5
> P$_{AOX1-Aca}$ (P$_{AOX1/Aca2}$)
AGATCTAACATCCAAAGACGAAAGGTTGAATGAAACCTTTTGCCATCCGACATCCACAGGTCCATTCTCACACATAAG
TGCCAAACGCAACAGGAGGGATACACTAGCAGCAGCCGTTGCAAACGCAGGACCTCCACTCTCTCTCCTCAAC
ACCCACTTTTGCCATCGAAAAACCAGCCAGTTATTGGGCTTGAGCTCGCTCATTCCAATTCCTCTATTAGGCT
ACTAACACCATGACTTTATTAGCCTGTCTATCCTGGCCCCCCGGCGAGGTTCATGTTGTTATTCCGAATGCAACAA
GCTCCGCATTACACCCGAACATCACTCCAGATGAGGGCTTTCTGAGTGTGGGTCAAATAGTTTCATGTTCCCAAATG
GCCCAAAACTGACAGTTTAAACGCTGTCTTGGAACCTAATATGACAAAAGCGTGATCTCATCCAAGATGAACTAAGTTT
GGTTCGTTGAAATGCTAACGGCCAGTGCCTATTGTAGACGTCAACCAAGTCGGCATACCGTTTGTCTGTTTGGTATT
GATTGACGAATGCTCAAAATAATCTCATTAAGCTTAGCGCAGTCTCTATCGCTTCTGAACCCGGTGCACCTGTGC
CGAAACGCAAATGGGGAAACACCCGCTTTTGGATGATTATGCATTGTCTCCACATTGTCTCCAAGATTCTGGTG
GGAATACTGCTGATAGCCTAAGTTCATGATCAAAATTTAACTGTCTAACCCCTACTTGACAGCAATATATAAACAGAA
GGAAGCTGCCCTGTCTTAAACCTTTTTTTTATCATCATTTACTTTCATAATTGGACTGGTTCCAATTGACAA
GCTTTTGATTTAACGACTTTAACGACAACTGAGAAGATCAAAAACAACTAATTATTCGAAACG

\* Modified positions in the design of AOX1 promoter variants are represented with bold and underlined characters.

FIG. 6

SEQUENCE LISTING

<160> NUMBER OF SEQ ID NOS: 29

<210> SEQ ID NO 1
<211> LENGTH: 870
<212> TYPE: DNA
<213> ORGANISM: Pichia pastoris

<400> SEQUENCE: 1

| | | | | | |
|---|---|---|---|---|---|
| acacataagt | gccaaacgca | acaggagggg | atacactagc | agcagaccgt | tgcaaacgca | 60 |
| ggacctccac | tcctcttctc | ctcaacaccc | acttttgcca | tcgaaaaacc | agcccagtta | 120 |
| ttgggcttga | ttggagctcg | ctcattccaa | ttccttctat | taggctacta | acaccatgac | 180 |
| tttattagcc | tgtctatcct | ggcccccctg | gcgaggttca | tgtttgttta | tttccgaatg | 240 |
| caacaagctc | cgcattacac | ccgaacatca | ctccagatga | gggctttctg | agtgtggggt | 300 |
| caaatagttt | catgttcccc | aaatggccca | aaactgacag | tttaaacgct | gtcttggaac | 360 |
| ctaatatgac | aaaagcgtga | tctcatccaa | gatgaactaa | gtttggttcg | ttgaaatgct | 420 |
| aacggccagt | tggtcaaaaa | gaaacttcca | aaagtcggca | taccgtttgt | cttgtttggt | 480 |
| attgattgac | gaatgctcaa | aaataatctc | attaatgctt | agcgcagtct | ctctatcgct | 540 |
| tctgaacccc | ggtgcacctg | tgccgaaacg | caaatgggga | acacccgct | ttttggatga | 600 |
| ttatgcattg | tctccacatt | gtatgcttcc | aagattctgg | tgggaatact | gctgatagcc | 660 |
| taacgttcat | gatcaaaatt | taactgttct | aaccccctact | tgacagcaat | atataaacag | 720 |
| aaggaagctg | ccctgtctta | aacctttttt | tttatcatca | ttattagctt | actttcataa | 780 |
| ttgcgactgg | ttccaattga | caagcttttg | attttaacga | cttttaacga | caacttgaga | 840 |
| agatcaaaaa | acaactaatt | attcgaaacg | | | | 870 |

<210> SEQ ID NO 2
<211> LENGTH: 940
<212> TYPE: DNA
<213> ORGANISM: Artificial Sequence
<220> FEATURE:
<223> OTHER INFORMATION: P AOX1-mod (P mAOX1)

<400> SEQUENCE: 2

| | | | | | |
|---|---|---|---|---|---|
| agatctaaca | tccaaagacg | aaaggttgaa | tgaaacctttt | ttgccatccg | acatccacag | 60 |
| gtccattctc | acacataagt | gccaaacgca | acaattccgt | tcgtccgatt | agcagaccgt | 120 |
| tgcaaacgca | ggacctccac | accccaatat | tatttggggt | acttttgcca | tcgaaaaacc | 180 |
| agcccagtta | ttgggcttga | ttggagctcg | ctcattccaa | ttccttctat | taggctacta | 240 |
| acaccatgac | tttattagcc | tgtctatcct | ggcccccctg | gcgaggttca | tgtttgttta | 300 |
| tttccgaatg | ccctctcgtc | cgggcttttt | ccgaacatca | ctccagatga | gggcgacccc | 360 |
| acatttttttt | tttgaccccca | catgttcccc | aaatggccca | aaactgacag | tttaaacgct | 420 |
| gtcttggaac | ctaatatgac | aaaagcgtga | tctcatccaa | gatgaactaa | gtttggttcg | 480 |
| ttgaaatgct | aacggccagt | gcctattgta | gacgtcaacc | caagtcggca | taccgtttgt | 540 |
| cttgtttggt | attgattgac | gaatgctcaa | aaataatctc | attaatgctt | agcgcagtct | 600 |
| ctctatcgct | tctgaacccc | ggtgcacctg | tgccgaaaca | tattccgttc | gtccgaatct | 660 |
| ttttggatga | ttaaccccaa | tacattttgg | ggttgcttcc | aagattctgg | tgggaatact | 720 |
| gctgatagcc | taacgttcat | gatcaaaatt | taactgttct | aaccccctact | tgacagcaat | 780 |
| atataaacag | aaggaagctg | ccctgtctta | aacctttttt | tttatcatca | ttattagctt | 840 |
| actttcataa | ttgcgactgg | ttccaattga | caagcttttg | attttaacga | cttttaacga | 900 |

| | |
|---|---:|
| caacttgaga agatcaaaaa acaactaatt attcgaaacg | 940 |

<210> SEQ ID NO 3
<211> LENGTH: 940
<212> TYPE: DNA
<213> ORGANISM: Artificial Sequence
<220> FEATURE:
<223> OTHER INFORMATION: P AOX1-Cat2 (P AOX1/Cat8-L2)

<400> SEQUENCE: 3

| | |
|---|---:|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg ccctctcgtc cgggcttttt ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| ttttggatga ttatgcattg tctccacatt gtatgcttcc aagattctgg tgggaatact | 720 |
| gctgatagcc taacgttcat gatcaaaatt taactgttct aaccoctact tgacagcaat | 780 |
| atataaacag aaggaagctg ccctgtctta aacctttttt tttatcatca ttattagctt | 840 |
| actttcataa ttgcgactgg ttccaattga caagcttttg attttaacga cttttaacga | 900 |
| caacttgaga agatcaaaaa acaactaatt attcgaaacg | 940 |

<210> SEQ ID NO 4
<211> LENGTH: 940
<212> TYPE: DNA
<213> ORGANISM: Artificial Sequence
<220> FEATURE:
<223> OTHER INFORMATION: P AOX1-Cat3 (P AOX1/Cat8-L3)

<400> SEQUENCE: 4

| | |
|---|---:|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaaca tattccgttc gtccgaatct | 660 |
| ttttggatga ttatgcattg tctccacatt gtatgcttcc aagattctgg tgggaatact | 720 |

```
gctgatagcc taacgttcat gatcaaaatt taactgttct aacccctact tgacagcaat    780
atataaacag aaggaagctg ccctgtctta aaccttttt tttatcatca ttattagctt     840
actttcataa ttgcgactgg ttccaattga caagcttttg attttaacga cttttaacga   900
caacttgaga agatcaaaaa acaactaatt attcgaaacg                          940

<210> SEQ ID NO 5
<211> LENGTH: 940
<212> TYPE: DNA
<213> ORGANISM: Artificial Sequence
<220> FEATURE:
<223> OTHER INFORMATION: P AOX1-Aca (P AOX1/Aca2)

<400> SEQUENCE: 5
agatctaaca tccaaagacg aaaggttgaa tgaaaccttt ttgccatccg acatccacag     60
gtccattctc acacataagt gccaaacgca acaggagggg atacactagc agcagaccgt   120
tgcaaacgca ggacctccac tcctcttctc ctcaacaccc acttttgcca tcgaaaaacc   180
agcccagtta ttgggcttga ttggagctcg ctcattccaa ttccttctat taggctacta   240
acaccatgac tttattagcc tgtctatcct ggccccctg gcgaggttca tgtttgttta    300
tttccgaatg caacaagctc cgcattacac ccgaacatca ctccagatga gggctttctg   360
agtgtggggt caaatagttt catgttcccc aaatggccca aaactgacag tttaaacgct   420
gtcttggaac ctaatatgac aaaagcgtga tctcatccaa gatgaactaa gtttggttcg   480
ttgaaatgct aacggccagt gcctattgta gacgtcaacc caagtcggca taccgtttgt   540
cttgtttggt attgattgac gaatgctcaa aaataatctc attaatgctt agcgcagtct   600
ctctatcgct tctgaacccc ggtgcacctg tgccgaaacg caaatgggga acacccgct    660 ttttggatga ttatgcattg tctccacatt gtatgcttcc aagattctgg tgggaatact   720
gctgatagcc taacgttcat gatcaaaatt taactgttct aacccctact tgacagcaat   780
atataaacag aaggaagctg ccctgtctta aaccttttt tttatcatca ttattagctt    840
actttcataa ttgcgactgg ttccaattga caagcttttg attttaacga cttttaacga   900
caacttgaga agatcaaaaa acaactaatt attcgaaacg                          940

<210> SEQ ID NO 6
<211> LENGTH: 14
<212> TYPE: DNA
<213> ORGANISM: Artificial Sequence
<220> FEATURE:
<223> OTHER INFORMATION: Cat8 transcription factor binding site

<400> SEQUENCE: 6
ttccgttcgt ccga                                                      14

<210> SEQ ID NO 7
<211> LENGTH: 14
<212> TYPE: DNA
<213> ORGANISM: Artificial Sequence
<220> FEATURE:
<223> OTHER INFORMATION: Cat8 transcription factor binding site

<400> SEQUENCE: 7
cctctcgtcc gggc                                                      14

<210> SEQ ID NO 8
<211> LENGTH: 21
<212> TYPE: DNA
<213> ORGANISM: Artificial Sequence
```

```
<220> FEATURE:
<223> OTHER INFORMATION: Aca1/Aca2 transcription factor binding site

<400> SEQUENCE: 8
gcctattgta gacgtcaacc c                                              21

<210> SEQ ID NO 9
<211> LENGTH: 20
<212> TYPE: DNA
<213> ORGANISM: Artificial Sequence
<220> FEATURE:
<223> OTHER INFORMATION: Adr1 transcription factor binding site

<400> SEQUENCE: 9
accccaatat tatttggggt                                                20

<210> SEQ ID NO 10
<211> LENGTH: 26
<212> TYPE: DNA
<213> ORGANISM: Artificial Sequence
<220> FEATURE:
<223> OTHER INFORMATION: Adr1 transcription factor binding site

<400> SEQUENCE: 10
gaccccacat ttttttttg acccca                                          26

<210> SEQ ID NO 11
<211> LENGTH: 20
<212> TYPE: DNA
<213> ORGANISM: Artificial Sequence
<220> FEATURE:
<223> OTHER INFORMATION: Adr1 transcription factor binding site

<400> SEQUENCE: 11
accccaatac attttggggt                                                20

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
ctcagatcta acatccaaag acgaaagg                                       28

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ctgagcactg cacgccgtag gt                                             22

<210> SEQ ID NO 14
<211> LENGTH: 35
<212> TYPE: DNA
<213> ORGANISM: Artificial Sequence
<220> FEATURE:
<223> OTHER INFORMATION: Primer

<400> SEQUENCE: 14
attccgttcg tccgattagc agaccgttgc aaacg                               35
```

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
aatcggacga acggaattgt tgcgtttggc acttatg        37

<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
accccaatat tatttggggt acttttgcca tcgaaaaac        39

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
accccaaata atattggggt gtggaggtcc tgcgtttg        38

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
cctctcgtcc gggcttttc cgaacatcac tccag        35

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
gaaaaagccc ggacgagagg gcattcggaa ataaacaaac        40

<210> SEQ ID NO 20
<211> LENGTH: 44
<212> TYPE: DNA
<213> ORGANISM: Artificial Sequence
<220> FEATURE:
<223> OTHER INFORMATION: Primer

<400> SEQUENCE: 20
gaccccacat tttttttttg accccacatg ttccccaaat ggcc        44

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
tggggtcaaa aaaaaaatgt ggggtcgccc tcatctggag tgatg                45

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
gcctattgta gacgtcaacc caagtcggca taccgtttgt c                    41

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
gggttgacgt ctacaatagg cactggccgt tagcatttc                       39

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
catattccgt tcgtccgaat ctttttggat gattatgc                        38

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
attcggacga acggaatatg tttcggcaca ggtgcaccg                       39

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
accccaatac attttggggt tgcttccaag attctggtgg                      40

<210> SEQ ID NO 27
<211> LENGTH: 41
<212> TYPE: DNA
<213> ORGANISM: Artificial Sequence
<220> FEATURE:
<223> OTHER INFORMATION: Primer

<400> SEQUENCE: 27
accccaaaat gtattggggt taatcatcca aaaagcgggt g                    41

<210> SEQ ID NO 28

```
<211> LENGTH: 42
<212> TYPE: DNA
<213> ORGANISM: Artificial Sequence
<220> FEATURE:
<223> OTHER INFORMATION: Primer

<400> SEQUENCE: 28
caaaaaacaa ctaattattc gaaacgaatg gtgagcaagg gc                             42

<210> SEQ ID NO 29
<211> LENGTH: 28
<212> TYPE: DNA
<213> ORGANISM: Artificial Sequence
<220> FEATURE:
<223> OTHER INFORMATION: Primer

<400> SEQUENCE: 29
cgaggtacct tacttgtaca gctcgtcc                                            28
```

MODIFIED AOX1 PROMOTER VARIANTS

CROSS REFERENCE TO THE RELATED APPLICATIONS

This application is the national phase entry of International Application No. PCT/TR2019/050783, filed on Sep. 23, 2019, which is based upon and claims priority to Turkish Patent Application No. 2018/13790, filed on Sep. 24, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBUY128_SL.txt and is 11,461 bytes in size.

TECHNICAL FIELD

The invention is related to original alcohol oxidase 1 (AOX1) gene promoter variants that have been enhanced or have re-designed regulation mechanisms that use ethanol as a sole carbon and energy source by promoter engineering design.

BACKGROUND

The productivity of a production process is an important criterion in industrial biotechnology applications. The capacity of the host microorganism to be able to produce the desired recombinant protein is dependent on the promoter architecture. Promoter genes are DNA nucleotide sequences that initiate and continue recombinant protein synthesis within the promoter architecture and that are necessary upstream DNA elements for protein expression. The number, quality, and functional position of the transcription factor binding sites available on promoter genes, the transcription factors that bind to these positions, and the interaction between them are the fundamental components of the promoter architecture. The strength of the promoter genes determines the recombinant protein production capacity of the host cells. The ideal recombinant protein production system is one that carries out production with high yield and in a controlled manner under a strong and regulated promoter gene. The regulated promoters enable the cell growth phase and the r-protein production phases to be separated from each other, thereby enhancing the control potential of the process. Moreover, the negative effects of the accumulation of recombinant proteins in the bioreactor on the growth of cells and their viability are also prevented by separating the two phases.

Industrial recombinant protein production with the yeast *Pichia pastoris* (*P. pastoris*) started in 1981 and in the last 10 years this has been the yeast on which most research was conducted. The phytase (Phytex, Sheridan, IN, USA) used in the feed industry, trypsin for proteomics studies (Roche Applied Science, GERMANY), nitrate reductase for water analysis and treatment (The Nitrate Elimination Co., Lake Linden, MI, USA), phospholipase C used in degumming of vegetable oils (Verenium, San Diego, CA, USA/DSM, Holland), collagen used in health research and as dermal filling (Fibrogen, San Francisco, CA, USA), and proteinase K (Thermo Scientific, Waltham, MA, USA) are recombinant proteins that are already being produced with the prior art by *P. pastoris* (Ahmad et al., 2014). The first biopharmaceutical product, KALBITOR® (ecallantide) approved by the FDA (USA), was released for sale in the year 2009. Jetrea® that is being produced with *P. pastoris* has also been approved by FDA and EMA (EU); and studies to develop new production methods for biopharmaceuticals and their approval applications are being continued.

*P. pastoris* is a methylotrophic yeast and it can grow by using methanol as a sole carbon source. Due to their methylotrophic nature, the genes in the methanol utilization pathway are expressed in high amounts, and the most commonly used and the strong AOX1 promoter of *P. pastoris*, $P_{AOX1}$, has been obtained from the methanol utilization pathway. The AOX1 enzyme catalyzes the oxidation of methanol to formaldehyde which is the first step in methanol utilization. AOX1 promoter ($P_{AOX1}$) is strongly induced in the presence of methanol and is repressed with different carbon sources such as ethanol, glucose, and glycerol. However, induction of $P_{AOX1}$ with methanol, that is a toxic alcohol, causes risks in bioprocess operations and the possibility that there may be methanol residue in recombinant proteins that have been produced for the food and pharmaceutical industries limits the usage of this promoter. The prevalent usage of crude enzymes that have low purity levels in the food industry limits the usage of methanol due to the increasing purification costs of recombinant protein products that are to be used in the food industry. While the threshold limit value (TLV) permitted for methanol in the working environment of the National Institute for Occupational Safety and Health (NIOSH), USA, is 200 ppm, this value for ethanol is 1000 ppm. Moreover, while the lethal dose of methanol is 0.3-1 g/kg, the lethal dose of ethanol is 7.060 g/kg. Ethanol is one of the first traditional biotechnological products produced in the history of humanity; and it is known to be safe as it has been used for many years in the chemical, pharmaceutical and food industries and it does not necessitate special precautions in terms of safe process applications.

Promoter genes have been identified by determining the functions of gene sequences in the genome of yeast *P. pastoris* and the wild-type or modified promoter gene sequences have been patented due their industrial potentials.

In the patent numbered U.S. Pat. No. 6,730,499 B1 of the prior art, the *P. pastoris* formaldehyde dehydrogenase (FLD1) promoter that is induced with methanol and/or methylamine has been disclosed. In said patent it is suggested that as the FLD1 promoter can perform production at a comparable level with the $P_{AOX1}$, it can be an alternative to $P_{AOX1}$. *P. pastoris* translation elongation factor (TEF) promoter gene and the recombinant protein production method with this constitutive promoter has protected with the patent numbered U.S. Pat. No. 7,816,509B2. *P. pastoris* wild-type ADH1 gene and the recombinant protein production processes with this gene has been patented with the patent numbered U.S. Pat. No. 8,222,386B2. Regulated GUT1 (glycerol kinase) promoter gene of the yeast *P. pastoris* has been patented with the patent numbered U.S. Pat. No. 8,785,613B2.

In the patent application numbered WO 2017/021541 A1 of the prior art, *P. pastoris* high-affinity glucose transporter (GTH1) gene promoter (pG1) variants (pG1-x) that are formed by the deletion, insertion or substitution mutations are described.

*P. pastoris* DAS promoter variants have been patented with the patent numbered US20110129874A1. These variants have been obtained by the deletion of some promoter gene regions or the insertion of some upstream activating sequence (UAS) gene elements located inside the promoter.

Mutant AOX1 promoters have been patented with the patent numbered U.S. Pat. No. 9,279,129B2. In this study, the transcription factor binding sites of Hap1, Hsf, Hap234, abaA, Stre, Rapt, Adr1, Mat1 MC, Gcr1 and QA-IF located on promoter gene have been identified and these sequences have been deleted or duplicated to create AOX1 mutants that display activity at a rate of 6% to 160% of the wild-type AOX1 promoter (Hartner et al. 2008).

The present invention relates to original alcohol oxidase 1 (AOX1) gene promoter variants that have been enhanced or have modified regulation mechanism.

SUMMARY

The main aim of the present invention is to provide genetic tools for enabling high yield recombinant protein production under controlled bioprocess conditions, in industrial biotechnology applications. The most important genetic tool to achieve high-yield bioprocess is strong promoters. The promoter variants subject to the present invention are original AOX1 promoter variants which provide enhanced production capacities in comparison to wild-type $P_{AOX1}$ under both methanol and ethanol induction conditions.

The fundamental advantages of the promoter variants subject to the present invention are that they are strong and regulated systems. Besides this, $P_{AOX1\text{-}Cat3}$ ($P_{AOX1/Cat8\text{-}L3}$) and $P_{AOX1\text{-}mod}$ ($P_{mAOX1}$) variants subject to the present invention are induced with ethanol which is normally a repressor of the wild-type AOX1 promoter. Ethanol provides important advantages for food and pharmaceutical industries as it is a cheap carbon source and it does not create toxicity risks against people who work in the production process.

With the promoter variants subject to the present invention, recombinant protein can be produced at higher yield than systems based on the wild-type AOX1 promoter for bioprocesses developed using methanol in the industry. Providing efficient process control by means of regulating active (on) and inactive (off) states of promoters with different carbon sources, enables to provide process requirements such as high product yield, product stability and production of toxic proteins to the cell. The present invention has a potential to provide both cost and time advantages in industrial biotechnology processes.

BRIEF DESCRIPTION OF THE DRAWINGS

FIG. 2 shows the nucleic acid sequence of $P_{AOX1\text{-}wt}$ (SEQ ID NO: 1).

FIG. 3 shows the nucleic acid sequence of $P_{AOX1\text{-}mod}$ ($P_{mAOX1}$) (SEQ ID NO: 2) with identification of the modified positions.

FIG. 4 shows the nucleic acid sequence of $P_{AOX1\text{-}Cat2}$ ($P_{AOX1/Cat8\text{-}L2}$) (SEQ ID NO: 3) with identification of the modified positions.

FIG. 5 shows the nucleic acid sequence of $P_{AOX1\text{-}Cat3}$ ($P_{AOX1/Cat8\text{-}L3}$) (SEQ ID NO: 4) with identification of the modified positions.

FIG. 6 shows the nucleic acid sequence of $P_{AOX1\text{-}Aca}$ ($P_{AOX1/Aca2}$) (SEQ ID NO: 5) with identification of the modified positions.

DETAILED DESCRIPTION OF THE EMBODIMENTS

Figure 1:
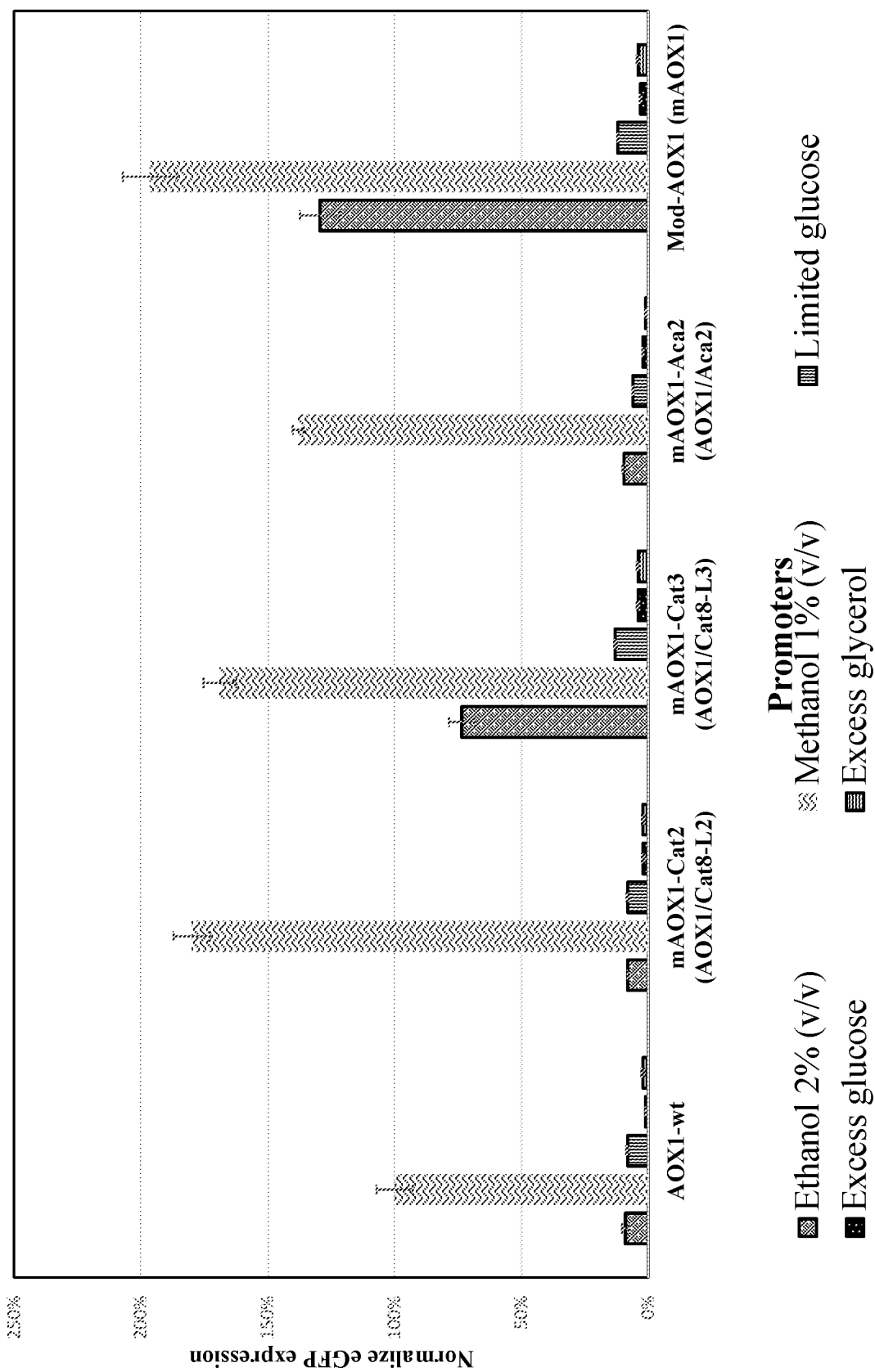
FIG. 1 shows normalized eGFP expressions of P. pastoris strains with respect to eGFP expression in the cells constructed with $P_{AOX1\text{-}wt}$ (%) M, constructed with the original AOX1 promoter variants and for comparison with the cells constructed with $P_{AOX1\text{-}wt}$ in different carbon sources.

Invention is related to the Pichia pastoris alcohol oxidase 1 (AOX1) promoter variants including at least one mutation within nucleotides 1 to 840 (−940 to −100) of the wild-type P. pastoris AOX1 promoter (SEQ ID NO: 1), under ethanol and methanol induction conditions.

The AOX1 promoter variants subject to the present invention is constructed by the method comprising the process steps of integration of transcription factor binding sites that are not naturally found on the P. pastoris wild-type AOX1 promoter by the substitution of the nucleotides located in the functionally targeted regions of the AOX1 promoter.

Two aspects that are required for the invention are:
  (i) Design of the transcription-factor-binding-site (TFBS) modification, and
  (ii) Selection of the position to be integrated to the P. pastoris AOX1 promoter via function analysis.

The method of designing promoter variant's Pichia pastoris alcohol oxidese (AOX1) promoter further includes a mutation selecting from the group consisting of: a) integration of a Cat8 transcription factor binding site (TFBS), particularly integration of the "TTCCGTTCGTCCGA" gene sequence (SEQ ID NO: 6) or other gene sequences that show at least 80% similarity with this sequence, at any position within nucleotides 94 to 110 (−847 to −831), 141 to 160 (−800 to −781), 312 to 330 (−629 to −611), 355 to 380 (−586 to −561), 501 to 521 (−440 to −420); 640 to 658 (−301 to −283), 674 to 693 (−267 to −248), and 1 to 840 (−940 to −100); b) integration of Aca1 or Aca2 TFBS particularly integration of the "GCCTATTGTAGACGTCAACCC" nucleotide sequence (SEQ ID NO: 8) or other gene sequences showing at least 80% similarity with this sequence at any position between the nucleotides 1 to 840 (−940 to −100); c) mutations specified with SEQ ID NO: 2 within nucleotides 94 to 693 (−847 to −248) and combinations thereof.

Promoter variant construction is performed by nucleotide mutations which are deletion, substitution, insertion and or inversion.

The efficiency of the production process is an important criterion in industrial biotechnology applications. The capacity of the host microorganism to be able to produce the desired recombinant protein is dependent on the promoter architecture. The ideal production system is a system which allows high yield production in a controlled manner by a strong and regulated promoter gene. The regulated promoters enable the separation of the cell growth phase and the recombinant protein production phase from each other, thereby increasing the control potential of the process. Moreover, by separating the two phases the effect of recombinant protein accumulation on cell growth and viability is also prevented.

In P. pastoris, the AOX1 promoter system, $P_{AOX1}$, is commonly used. When $P_{AOX1}$ is used, the need to feed toxic alcohol methanol into the bioreactor creates risks. The possibility that there may remain methanol residue in recombinant proteins that have been produced for the food and pharmaceutical industry limits the usage of this method. Ethanol, is one of the first traditional biotechnological products that have been produced in history of humanity. Ethanol is known to be non-hazardous as it has been used for many years in the chemical, pharmaceutical and food industries and it does not necessitate special precautions to be taken in terms of safe process applications. The $P_{AOX1\text{-}mod}$ ($P_{mAOX1}$) and $P_{AOX1}$-Cat3 ($P_{AOX1/Cat8\text{-}L3}$); subject to the present invention can provide respectively, 130% and 74% of the production capacity of the methanol induced wild-type $P_{AOX1}$, by using ethanol instead. In other words, while wild-type $P_{AOX1}$ is repressed with ethanol and does not show any activity, the promoter variants $P_{AOX1\text{-}mod}$ ($P_{mAOX1}$) and $P_{AOX1\text{-}Cat3}$ ($P_{AOX1/Cat8\text{-}L3}$) subject to the present invention can perform recombinant protein production with ethanol. As ethanol is the inducing agent of the promoter variants subject to the present invention which are $P_{AOX1\text{-}mod}$ ($P_{mAOX1}$) and $P_{AOX1\text{-}Cat3}$ ($P_{AOX1/Cat8\text{-}L3}$), this increases the industrial significance of the variants subject to the present invention as ethanol is both cheap and has a nontoxic and non-hazardous nature.

The important, novel feature of the promoter variants subject to the present invention is that they are stronger than the P. pastoris wild-type AOX1 promoter ($P_{AOX1\text{-}wt}$) and as a result they can perform higher amounts of recombinant protein production. The promoter variants subject to the present invention can provide 38%-97% more recombinant protein production in comparison to the P. pastoris wild-type $P_{AOX1}$ under methanol induction. Wild-type $P_{AOX1}$ controlled recombinant protein production under methanol induction has been carried out with the yeast P. pastoris since 1981. All of the promoter variants, $P_{AOX1\text{-}mod}$ ($P_{mAOX1}$), $P_{AOX1\text{-}Cat2}$ ($P_{AOX1/Cat8\text{-}L2}$), $P_{AOX1\text{-}Cat3}$ ($P_{AOX1/Cat8\text{-}L3}$), and $P_{AOX1\text{-}Aca}$ ($P_{AOX1/Aca2}$), subject to the present invention have higher recombinant protein production capacity in comparison to wild-type $P_{AOX1}$ under methanol induction condition. Enhanced AOX1 promoter variants that have been developed with promoter engineering designs provide significant advantages as they have higher production capacity in methanol based bioprocess applications in which industry has long-standing experience and technical knowledge. Production applications that can be performed with high yield and effective process control applications have the potential to provide advantages both in terms of saving cost and time.

The promoter variants subject to the present invention consist of 940 nucleotide sequence. When the positions of nucleotides are counted from the first nucleotide at the 5' end, the position of a nucleotide is expressed with a positive number value. However, nucleotides on the promoter can also be determined based on the start of a coding sequence which locates at the end of the promoter, in such a case the first nucleotide (in our case nucleotide G) at the 3' end of the promoter is positioned at "−1", and the nucleotide positions continue to decrease towards the 5' end of the promoter gene, and the first nucleotide (in our case nucleotide A) at the 5' end of the gene is located at −940 base pair (bp) position.

When designing the AOX1 promoter variants subject to the present invention, as a method, the TFBS gene motifs that are not naturally found on the P. pastoris wild-type AOX1 promoter have been integrated to functionally determined positions by means of substitution of the nucleotides. In the present invention; $P_{AOX1\text{-}Cat2}$ ($P_{AOX1/Cat8\text{-}L2}$), $P_{AOX1\text{-}Cat3}$ ($P_{AOX1/Cat8\text{-}L3}$), $P_{AOX1\text{-}Aca}$ ($P_{AOX1/Aca2}$) and $P_{AOX1\text{-}mod}$ ($P_{mAOX1}$) variants have been designed and constructed by integrating Cat8 transcription factor binding sequence (TFBS) "TTCCGTTCGTCCGA" (SEQ ID NO: 6) (Roth et al., 2004), Adr1 TFBSs "ACCCCAATATTAT-TTGGGGT" (SEQ ID NO: 9), "GACCCCACAT-TTTTTTTTTGACCCCA" (SEQ ID NO: 10) and "ACCC-CAATACATTTGGGGT" (SEQ ID NO: 11) (core sequences are represented by bold and underlined characters) (Cheng vd., 1994) since Cat8 and Adr1 transcription factors are known to be as important activators of ethanol utilization pathway genes of Saccharomyces cerevisiae- important ethanol (ethyl alcohol) producing yeast in traditional biotechnology-; and the sequence "GCCTATTGTA-GACGTCAACCC" (SEQ ID NO: 8) which forms the Aca1/Aca2 TFBS identified on P. pastoris ADH2 promoter that is responsible for ethanol utilization.

The original AOX1 promoter variants subject to the present invention, allow to the design of bioreactor operation conditions for the recombinant protein production process with an original-novel-strategic method. By using the induction and repression properties of the promoter, bioreactor feeding strategies which can be regulated under the original AOX1 promoter variants can be developed. In the first phase of the bioreactor operation, by feeding glucose or glycerol that repress the promoter, thereby stopping the recombinant protein production results in high cell density cultures, in the second phase feeding ethanol or methanol in increasing concentrations can provide significant promoter induction and effective process control for high cell density recombinant protein production process. Providing an effective process control mechanism and separating the production phase from the cell growth phase have significant advantages in specific cases depending on the features of the heterologous protein to be produced. These advantages are obtaining high protein yield at the end of the process, enhanced product stability, and recombinant protein production in cases where the protein to be expressed is toxic.

The detailed description of the AOX1 promoter variants subject to the present invention has been provided below.

Promoter Variant-1 Design: $P_{AOX1\text{-}mod}$ ($P_{mAOX1}$) (SEQ ID NO: 2)

When the $P_{AOX1\text{-}mod}$ ($P_{mAOX1}$) promoter variant is being designed with promoter engineering principles, it is constructed by integrating TFBSs that are important in ethanol induction to the functionally critical points of the promoter that is normally induced with methanol; and as a result the promoter's regulation mechanism is converted from methanol to ethanol. At the same time, the $P_{AOX1\text{-}mod}$ ($P_{mAOX1}$) promoter variant subject to the present invention maintains methanol inducible feature and, moreover when it is induced with methanol it can even produce approximately 2-times more than the wild-type AOX1 promoter. In the design of $P_{AOX1\text{-}mod}$ ($P_{mAOX1}$) 7 different nucleotide stretches on wild-type AOX1 promoter have been modified. Adr1 TFBS optimized for yeast S. cerevisiae has been integrated to 3 different positions, Cat8 TFBS optimized for yeast S. cerevisiae has been integrated to 3 different positions, and Aca1/Aca2 TFBS identified on P. pastoris wild-type ADH2 promoter has been integrated to one position. $P_{AOX1\text{-}mod}$ ($P_{mAOX1}$) gene sequence shows 89% identity with the wild-type $P_{AOX1}$ gene sequence. The $P_{AOX1\text{-}mod}$ ($P_{mAOX1}$) sequence has been given with SEQ ID NO: 2 and the integrated TFBSs are Cat8 TFBS, Adr1 TFBS and Aca1 TFBS. While wild-type AOX1 promoter is being repressed with ethanol, higher recombinant protein production capacities can be achieved with the designed $P_{AOX1}$-mod ($P_{mAOX1}$) variant under ethanol induction, in comparison to the recombinant protein production levels obtained with methanol induced wild-type $P_{AOX1}$. Besides this, the $P_{AOX1\text{-}mod}$ ($P_{mAOX1}$) promoter still sustain methanol inducible nature and can perform 97% more production with methanol than the wild-type AOX1 promoter.

Promoter Variant-2 Design: $P_{AOX1\text{-}Cat2}$ ($P_{AOX1/Cat8\text{-}L2}$) (SEQ ID NO: 3)

In the $P_{AOX1\text{-}Cat2}$ ($P_{AOX1/Cat8\text{-}L2}$) promoter variant design, the Mxr1 (Methanol expression regulator 1) TFBS located in the third row from the starting position of the promoter gene in the wild-type AOX1 promoter, has been substituted with, Cat8 TFBS sequence. Said promoter variant can perform 80% more recombinant protein production in methanol fermentation in comparison to the wild-type AOX1 promoter.

Promoter Variant-3 Design: $P_{AOX1\text{-}Cat3}$ ($P_{AOX1/Cat8\text{-}L3}$) (SEQ ID NO: 4)

The $P_{AOX1\text{-}Cat3}$ ($P_{AOX1/Cat8\text{-}L3}$) promoter variant has been constructed by substitution of Mxr1 TFBS located in the fifth row from the starting position of the promoter gene in the wild-type AOX1 promoter, with the Cat8 TFBS sequence. The regulation of the AOX1 promoter has been changed with the modification in a single gene region, and while $P_{AOX1}$ is repressed with ethanol, $P_{AOX1\text{-}Cat3}$ ($P_{AOX1/Cat8\text{-}L3}$) can perform 74% of the production capacity exhibited by $P_{AOX1}$ with methanol, using ethanol instead. Besides this, it doesn't lose its ability to be regulated with methanol and it can provide 69% more production under methanol induction in comparison to $P_{AOX1}$.

Promoter Variant-4 Design: $P_{AOX1\text{-}Aca}$ ($P_{AOX1/Aca2}$) (SEQ ID NO: 5)

Promoter variant $P_{AOX1\text{-}Aca}$ ($P_{AOX1/Aca2}$) has been designed with Aca1/2 TFBS integration which is not naturally found on the wild-type AOX1 promoter. $P_{AOX1\text{-}Aca}$ ($P_{AOX1/Aca2}$), can perform 38% more production with methanol induction in comparison to $P_{AOX1}$.

EXAMPLES

Example 1

Material and Method

Example 1.1

Designing AOX1 Promoter Variants and Cloning with the Reporter eGFP Gene

Two-step overlap extension polymerase chain reaction (OE-PCR) method was used for construction of AOX1 promoter variants and the designed primers given below the table have been used to construct $P_{AOX1\text{-}mod}$ ($P_{mAOX1}$), $P_{AOX1\text{-}Cat2}$ ($P_{AOX1/Cat8\text{-}L2}$), $P_{AOX1\text{-}Cat3}$ ($P_{AOX1/Cat8\text{-}L3}$), and $P_{AOX1\text{-}Aca}$ ($P_{AOX1/Aca2}$) promoter variants.

TABLE 1

The designed primer nucleotide sequences used for the integration of Adr1, Cat8 and Aca2 TFBSs to the designed promoter variants and for cloning the promoter variants with eGFP.

| Name of Primer | Primer Nucleotide Sequence | SEQ ID NO: |
|---|---|---|
| Forward $P_{AOX1}$ | CTCAGATCTAACATCCAAAGACGAAAGG | 12 |
| Reverse $P_{AOX1}$ | CTGAGCACTGCACGCCGTAGGT | 13 |
| Forward mAOX-AddCat8-1 | ATTCCGTTCGTCCGATTAGCAGACCGTTGCAAACG | 14 |
| Reverse mAOX-AddCat8-1 | AATCGGACGAACGGAATTGTTGCGTTTGGCACTTATG | 15 |
| Forward mAOX-AddAdr1-1 | ACCCCAATATTATTTGGGGTACTTTTGCCATCGAAAAAC | 16 |
| Reverse mAOX-AddAdr1-1 | ACCCCAAATAATATTGGGGTGTGGAGGTCCTGCGTTTG | 17 |
| Forward mAOX-AddCat8-2 | CCTCTCGTCCGGGCTTTTTCCGAACATCACTCCAG | 18 |
| Reverse mAOX-AddCat8-2 | GAAAAAGCCCGGACGAGAGGGCATTCGGAAATAAACAAAC | 19 |
| Forward mAOX-AddAdr1-2 | GACCCCACATTTTTTTTTGACCCCACATGTTCCCCAAATGGCC | 20 |
| Reverse mAOX-AddAdr1-2 | TGGGGTCAAAAAAAAAATGTGGGGTCGCCCTCATCTGGAGTGATG | 21 |
| Forward mAOX-AddAca2 | GCCTATTGTAGACGTCAACCCAAGTCGGCATACCGTTTGTC | 22 |
| Reverse mAOX-AddAca2 | GGGTTGACGTCTACAATAGGCACTGGCCGTTAGCATTTC | 23 |

TABLE 1-continued

The designed primer nucleotide sequences used for the integration of Adr1, Cat8 and Aca2 TFBSs to the designed promoter variants and for cloning the promoter variants with eGFP.

| Name of Primer | Primer Nucleotide Sequence | SEQ ID NO: |
|---|---|---|
| Forward mAOX-AddCat8-3 | CATATTCCGTTCGTCCGAATCTTTTTGGATGATTATGC | 24 |
| Reverse mAOX-AddCat8-3 | ATTCGGACGAACGGAATATGTTTCGGCACAGGTGCACCG | 25 |
| Forward mAOX-AddAdr1-3 | ACCCCAATACATTTTGGGGTTGCTTCCAAGATTCTGGTGG | 26 |
| Reverse mAOX-AddAdr1-3 | ACCCCAAAATGTATTGGGGTTAATCATCCAAAAAGCGGGTG | 27 |
| Forward_eGFP | CAAAAAACAACTAATTATTCGAAACGAATGGTGAGCAAGGGC | 28 |
| Reverse_eGFP | CGAGGTACCTTACTTGTACAGCTCGTCC | 29 |

The enhanced green fluorescent protein (eGFP) gene has been used as a reporter for determining the gene expression level under the AOX1 promoter variant. The eGFP gene and AOX1 promoter variants gene were amplified by OE-PCR method using the primers given in the Table above. Any nucleotide addition between promoter and eGFP gene sequences were prevented. Amplified promoter variant and eGFP gene fragments were digested by using suitable restriction enzymes and cloned with ligation reaction to the vector which carries a Zeocin™ resistance gene and an AOX1 transcription terminator module.

Constructed plasmids were transformed to the chemically competent *Escherichia coli* DH5a cells that have been prepared with the calcium chloride method (Sambrook and Russell, 2001). Putative positive clones were selected using Zeocin™ containing selective LB agar media and following plasmid isolation constructed recombinant vectors were verified by gene sequencing analysis.

Example 1.2

Transformation of the Yeast *Pichia pastoris* with Recombinant Vectors Carrying Promoter Variants and the Evaluation of the Expression Capacities of Promoter Variants The recombinant vectors containing the AOX1 promoter variant and the eGFP reporter genes were linearized with Bg/II restriction enzyme according to the suggestions of the manufacturer and the competent *P. pastoris* X33 cells prepared with lithium chloride method were transfected with linearized gene fragments (Invitrogen, 2000). After regeneration, the transformants were inoculated into selective Zeocin™ containing YPD Agar medium. Following transformation, putative clones carrying the expression cassette comprising the promoter variant gene and the eGFP reporter gene was verified with colony PCR and at least 10 individuals were selected from each strain and used to evaluate the production capacities of promoter variants.

The expression cassette comprises at least one AOX1 promoter variant and at least a nucleic acid molecule encoding a protein (peptide) or functional nucleotide, said promoter variant and nucleic acid molecule form single- or multi-copy expression cassette. These Nucleic acid molecule and promoter are operably linked together.

The vector carrying the Zeocin™ resistance gene and an AOX1 transcription terminator module, comprises *Pichia pastoris* alcohol oxidase 1 (AOX1) promoter variant and at least a nucleic acid molecule in the expression cassette.

*Pichia pastoris* cells were precultivated in YP medium (10 g/L yeast extract, 20 g/L peptone) for 20 hours at 25° C. at 280 rpm before being transferred to the production medium. At the end of the precultivation, cells were harvested by centrifugation and transferred to the production medium. In order to evaluate the expression capacities of the promoter variants a minimal medium (6.3 g/L (NH$_4$)$_2$HPO$_4$; 0.8 g/L (NH$_4$) 2SO$_4$; 0.49 g/L MgSO$_4$*7H$_2$O; 2.64 g/L KCl; 0.0535 g/L CaCl$_2$*2H$_2$O; 22 g/L citric acid monohydrate; 1.47 ml/L PTM1; 2 ml/L biotin (0.2 g/L); 20 ml NH$_4$OH (25%)) including 5 different carbon sources separately was used. Different substrates used and the production parameters applied in the production trial were given in the table below. A production medium including m2p kit polysaccharide 25% (v/v) and 0.7% (v/v) enzyme (m2p-labs GmbH, Germany) mixture was used for limited glucose condition.

TABLE 2

Production test parameters applied in order to compare eGFP production capacities of promoter variants with *Pichia pastoris*.

| Condition | I D | Initial OD$_{600}$ Value | Production Substrate | Production Time |
|---|---|---|---|---|
| Excess glycerol | G | 0.1 | 2 g/L glycerol | 20 hours |
| Excess glucose | D | 0.1 | 2 g/L glycerol | 20 hours |
| Limited glucose | X | 1 | Limited glucose concentration | 20 hours |
| Methanol | M | 1 | 1% (v/v) methanol | 20 hours |
| Ethanol | E | 1 | 2% (v/v) ethanol | 20 hours |

The cells were cultured in 2 ml production media including different carbon source in 24 deep-well-plates (24 deep-well-plate, Whatman, UK)) for 20 hours at a mixing speed of 280 rpm and at a temperature of 25° C. At the end of the 20th hour, Pichia pastoris cells were diluted in a phosphate-buffered saline solution to the $OD_{600}$ value of 0.4.

Intracellular eGFP production values were determined by measuring average eGFP fluorescence per unit cell using Guava easyCyte™ (MilliPore) flow cytometry. In flow cytometry eGFP was stimulated at 488 nm and the emission value was collected at 525 nm. Fluorescence signal from 10,000 cells were taken into account in each measurement, using FSC and SSC values, cells which define the yeast cluster in the graphic were selected and the cells that show linear regression in terms of FSC-H and FSC-A values were gated to select singlets. Fluorescence intensity based on the cell volume and geometric mean of the gated population were used in eGFP fluorescence calculations for determination of the specific eGFP synthesis levels of the cells. Relative eGFP expression levels were calculated compared to eGFP expression under wild-type $P_{AOX1-wt}$ in 1% (v/v) methanol.

These cells comprise at least one Pichia pastoris alcohol oxidase 1 (AOX1) promoter variant. Said cell is a eukaryotic cell, particularly a yeast cell, preferably a methylotrophic yeast cell, preferably a yeast cell selected from the group consisting of Pichia, Candida, Hansenula and Toruplosis, especially a Pichia pastoris cell.

Recombinant proteins, peptide or functional nucleic acid are expressed by the following steps:

Production of AOX1 promoter variants,

Production of expression cassette with the addition of eGFP reporter gene,

Production of recombinant vector promoter variants,

Transformation of eukaryotic cells especially yeast cell, preferably a methylotrophic yeast cell, preferably a yeast cell selected from the group consisting of Pichia, Candida, Hansenula and Toruplosis, especially a Pichia pastoris cell with the recombinant vector and culturing the transformed cells in a suitable medium, Preferably inducible expression of said protein, peptide or functional nucleic acid molecule, Isolation of the produced protein, peptide or functional nucleic acid molecule.

Example 2

Results

The recombinant protein (eGFP) production under the promoter variants subject to the present invention were tested with shake flask bioreactor experiments. Production capacities of the designed promoter variants were compared with commonly used P. pastoris $P_{AOX1-wt}$, and the results are given in Table 3. Effect of different carbon sources on the activity of the promoter variants and thus efficiency of recombinant protein production were evaluated with 3 P. pastoris biological replicas. Productivities of promoter variants are given in the table below, eGFP production by $P_{AOX1-wt}$ under 1% (v/v) methanol induction was determined as 100 unit and productivities of variants were related to this value.

TABLE 3

The eGFP production capacities of the designed $P_{AOX1}$ variants in yeast P. pastoris with different carbon sources. E: 2% (v/v) ethanol, M: 1% (v/v) methanol, X: limited glucose, D: excess glucose (2 g/L), G: excess glycerol (2 g/L)

| $P_{AOX1}$ Variants | E | M | X | D | G |
|---|---|---|---|---|---|
| AOX1-wt | 9 ± 1 | 100 ± 7 | 8 ± 1 | 1 ± 0 | 2 ± 1 |
| mAOX1-Cat2 (AOX1/Cat8-L2) | 8 ± 0 | 180 ± 7 | 8 ± 0 | 2 ± 0 | 2 ± 0 |
| mAOX1-Cat3 (AOX1/Cat8-L3) | 74 ± 5 | 169 ± 6 | 13 ± 0 | 4 ± 0 | 4 ± 0 |
| mAOX1-Aca (AOX1/Aca2) | 10 ± 1 | 138 ± 2 | 6 ± 0 | 2 ± 0 | 1 ± 0 |
| Mod-AOX1 (mAOX1) | 130 ± 8 | 197 ± 11 | 12 ± 0 | 3 ± 0 | 4 ± 1 |

The recombinant protein (eGFP) production capacities of original AOX1 promoter variants have been significantly increased in comparison to the wild-type AOX1 promoter in defined minimal medium supplied with methanol. Promoter variants $P_{AOX1-Cat2}$ ($P_{AOX1/Cat8-L2}$), $P_{AOX1-Cat3}$ ($P_{AOX1/Cat8-L3}$), $P_{AOX1-Aca}$ ($P_{AOX1/Aca2}$) and $P_{AOX1-mod}$ ($P_{mAOX1}$) performed more than 80%, 69%, 38% and 97% eGFP production, respectively in comparison to $P_{AOX1-wt}$ in methanol fermentation. Besides this, whereas ethanol represses $P_{AOX1-wt}$ and thus recombinant protein production, the original promoter variants $P_{AOX1-Cat3}$ ($P_{AOX1/Cat8-L3}$) and $P_{AOX1-mod}$ ($P_{mAOX1}$) subject to the present invention are ethanol inducible and can perform 74% and 130% production capacity of methanol induced $P_{AOX1-wt}$ respectively, instead by using ethanol as a carbon and energy source. While the designed promoter variants can reach significantly high production capacities under ethanol or methanol induction in comparison to $P_{AOX1-wt}$ they still sustain their regulated nature by being repressed in the presence of glucose and glycerol. The recombinant protein production experiments that are conducted under laboratory scale conditions demonstrate industrial potential and significance of original AOX1 promoter variants in biotechnological processes.

REFERENCES

Ahmad, M., Hirz, M., Pichler, H., &Schwab, H. (2014). Protein expression in Pichia pastoris: recent achievements and perspectives for heterologous protein production. Applied microbiology and biotechnology, 98 (12), 5301-5317.

Cheng, C., Kacherovsky, N., Dombek, K. M., Camier, S., Thukral, S. K., Rhim, E., Young, E. T., 1994.Identification of potential target genes for Adr1p through characterization of essential nucleotides in UAS1. Mol. Cell. Biol. 14, 3842-52.

Hartner, F. S., Ruth, C., Langenegger, D., Johnson, S. N., Hyka, P., et al. (2008). Promoter library designed for fine-tuned gene expression in Pichia pastoris. Nucleic acids research, 36 (12), e76-e76.

Invitrogen (2010), EasySelect™ Pichia Expression Kit For Expression of Recombinant Proteins Using pPICZ and PPICZα in Pichia pastoris Roth, S., Kumme, J., and Schüller, H. J. (2004). Transcriptional activators Cat8 and Sip4 discriminate between sequence variants of the carbon source-responsive promoter element in the yeast Saccharomyces cerevisiae. Current genetics, 45 (3), 121-128.

Sambrook, J., Russell, D. W. (2001) "Molecular cloning: a library manual", $3^{rd}$edn., Cold Spring Harbor Library Press, Cold Spring Harbor, New York.

What is claimed is:

1. A *Pichia pastoris* alcohol oxidase 1 (AOX1) promoter variant, comprising at least one mutation within nucleotides 1 to 840 of a nucleic acid sequence of a wild-type *P. pastoris* AOX1 promoter, wherein the nucleic acid sequence of the wild type *P. pastoris* AOX1 promoter has the sequence of SEQ ID NO: 1;

the at least one mutation is selected from the group consisting of integration of a transcription factor binding site (TFBS) having the sequence of SEQ ID NO: 6, integration of a TFBS having the sequence of SEQ ID NO: 7, integration of a TFBS having the sequence of SEQ ID NO: 8, integration of a TFBS having the sequence of SEQ ID NO:

9, integration of a TFBS having the sequence of SEQ ID NO: 10 and integration of a TFBS having the sequence of SEQ ID NO: 11; and the *Pichia pastoris* AOX1 promoter variant is induced with one or more selected from the group consisting of ethanol and methanol.

2. The *Pichia pastoris* alcohol oxidase 1 (AOX1) promoter variant of claim 1, wherein a) integration of the TFBS having the sequence of SEQ ID NO: 6 or the integration of a TFBS having the sequence of SEQ ID NO: 7 is at any positions within nucleotides 94 to 110, 312 to 330, and 640 to 658 of SEQ ID NO: 1;

b) integration of the TFBS having the sequence of SEQ ID NO: 8 is at any positions between the nucleotides 501 to 521 of SEQ ID NO: 1; and c) integration of the TFBS having the sequence of SEQ ID NO: 9, integration of a TFBS having the sequence of SEQ ID NO: 10 or integration of a TFBS having the sequence of SEQ ID NO: 11 is at any positions within nucleotides 141 to 160, 355 to 380, and 674 to 693.

3. An expression cassette, comprising at least one of the *Pichia pastoris* AOX1 promoter variants of claim 1 and at least one nucleic acid molecule encoding a recombinant protein or a peptide, wherein the *Pichia pastoris* AOX1 promoter variant and the nucleic acid molecule form a single- or multi-copy expression cassette.

4. The expression cassette of claim 3, wherein the *Pichia pastoris* AOX1 promoter variant and the nucleic acid molecule are operably linked together.

5. A vector comprising the *Pichia pastoris* alcohol oxidase 1 (AOX1) promoter variant of claim 1 and at least one nucleic acid molecule encoding a recombinant protein or a peptide".

6. A cell comprising an expression cassette or a vector, wherein the expression cassette comprises at least one of the *Pichia pastoris* AOX1 promoter variants of claim 1 and at least one nucleic acid molecule encoding a recombinant protein or a peptide, and the vector comprises the *Pichia pastoris* alcohol oxidase 1 (AOX1) promoter variant and at least one nucleic acid molecule encoding the recombinant protein or the peptide.

7. The cell of claim 6, wherein the cell is a eukaryotic cell wherein the eukaryotic cell is a methylotrophic yeast cell, wherein the methylotrophic yeast cell is selected from the group consisting of *Pichia, Candida, Hansenula* and *Toruplosis*.

8. An expression method of a recombinant protein or a peptide comprising the following steps:

providing an expression cassette or a vector, wherein the expression cassette comprises at least one of the *Pichia pastoris* AOX1 promoter variants of claim 1 and at least one nucleic acid molecule encoding the recombinant protein or the peptide, wherein the *Pichia pastoris* AOX1 promoter variant and the nucleic acid molecule form a single- or multi-copy expression cassette, wherein the vector comprises the *Pichia pastoris* AOX1 promoter variant and at least one nucleic acid molecule;

transforming a cell with the vector or the expression cassette to obtain a transformed cell, wherein the transformed cell comprises at least one of the *Pichia pastoris* alcohol oxidase 1 (AOX1) promoter variants and the expression cassette or the vector;

culturing the transformed cell in a suitable medium;

inducing an expression of the recombinant protein or the peptide; and isolating the recombinant protein or the peptide.

9. The expression method of claim 8, wherein the cell is an eukaryotic cell, and the eukaryotic cell is a methylotrophic yeast cell selected from the group consisting of *Pichia, Candida, Hansenula* and *Toruplosis*.

10. The expression cassette of claim 3, wherein the a) integration of the TFBS having the sequence of SEQ ID NO: 6 or the integration of a TFBS having the sequence of SEQ ID NO: 7 is at any positions within nucleotides 94 to 110, 312 to 330, and 640 to 658 of SEQ ID NO: 1;
b) integration of the TFBS having the sequence of SEQ ID NO: 8 is at any positions between the nucleotides 501 to 521 of SEQ ID NO: 1; and
c) integration of the TFBS having the sequence of SEQ ID NO: 9, integration of a TFBS having the sequence of SEQ ID NO: 10 or integration of a TFBS having the sequence of SEQ ID NO: 11 is at any positions within nucleotides 141 to 160, 355 to 380, and 674 to 693.

11. The vector of claim 5, wherein in the *Pichia pastoris* AOX1 promoter variant
a) integration of the TFBS having the sequence of SEQ ID NO: 6 or the integration of a TFBS having the sequence of SEQ ID NO: 7 is at any positions within nucleotides 94 to 110, 312 to 330, and 640 to 658 of SEQ ID NO: 1;
b) integration of the TFBS having the sequence of SEQ ID NO: 8 is at any positions between the nucleotides 501 to 521 of SEQ ID NO: 1; and
c) integration of the TFBS having the sequence of SEQ ID NO: 9, integration of a TFBS having the sequence of SEQ ID NO: 10 or integration of a TFBS having the sequence of SEQ ID NO: 11 is at any positions within nucleotides 141 to 160, 355 to 380, and 674 to 693.

12. The cell of claim 6, wherein in the *Pichia pastoris* AOX1 promoter variant
a) integration of the TFBS having the sequence of SEQ ID NO: 6 or the integration of a TFBS having the sequence of SEQ ID NO: 7 is at any positions within nucleotides 94 to 110, 312 to 330, and 640 to 658 of SEQ ID NO: 1;
b) integration of the TFBS having the sequence of SEQ ID NO: 8 is at any positions between the nucleotides 501 to 521 of SEQ ID NO: 1; and
c) integration of the TFBS having the sequence of SEQ ID NO: 9, integration of a TFBS having the sequence of SEQ ID NO: 10 or integration of a TFBS having the sequence of SEQ ID NO: 11 is at any positions within nucleotides 141 to 160, 355 to 380, and 674 to 693.

13. The expression method according to of claim 8, wherein in the *Pichia pastoris* AOX1 promoter variant
a) integration of the TFBS having the sequence of SEQ ID NO: 6 or the integration of a TFBS having the sequence of SEQ ID NO: 7 is at any positions within nucleotides 94 to 110, 312 to 330, and 640 to 658 of SEQ ID NO: 1;
b) integration of the TFBS having the sequence of SEQ ID NO: 8 is at any positions between the nucleotides 501 to 521 of SEQ ID NO: 1; and
c) integration of the TFBS having the sequence of SEQ ID NO: 9, integration of a TFBS having the sequence of SEQ ID NO: 10 or integration of a TFBS having the sequence of SEQ ID NO: 11 is at any positions within nucleotides 141 to 160, 355 to 380, and 674 to 693.

14. The expression method of claim 8, wherein in the expression cassette, the *Pichia pastoris* AOX1 promoter variant and the nucleic acid molecule are operably linked together.

15. The *Pichia pastoris* alcohol oxidase 1 (AOX1) promoter variant of claim 1, wherein the *Pichia pastoris* AOX1 promoter variant has the sequence of SEQ ID NO: 5.

16. The *Pichia pastoris* alcohol oxidase 1 (AOX1) promoter variant of claim 1, wherein the *Pichia pastoris* AOX1 promoter variant has the sequence of SEQ ID NO: 4.

17. The *Pichia pastoris* alcohol oxidase 1 (AOX1) promoter variant of claim 1, wherein the *Pichia pastoris* AOX1 promoter variant has the sequence of SEQ ID NO: 3.

18. The *Pichia pastoris* alcohol oxidase 1 (AOX1) promoter variant of claim 1, wherein the *Pichia pastoris* AOX1 promoter variant has the sequence of SEQ ID NO: 2.

* * * * *